(12) United States Patent
Shin et al.

(10) Patent No.: US 11,091,718 B2
(45) Date of Patent: Aug. 17, 2021

(54) IONIC LIQUID CONTAINING DIVALENT CATION AND MONOVALENT ANION AND LUBRICANT COMPOSITION COMPRISING SAME

(71) Applicants: SK INNOVATION CO., LTD., Seoul (KR); SK LUBRICANTS CO., LTD., Seoul (KR)

(72) Inventors: Sang Hye Shin, Daejeon (KR); Ha Na Song, Daejeon (KR); Yu Na Shim, Daejeon (KR); Sun Ae Hwang, Daejeon (KR)

(73) Assignees: SK INNOVATION CO., LTD., Seoul (KR); SK LUBRICANTS CO., LTD., Seoul (KR)

( * ) Notice: Subject to any disclaimer, the term of this patent is extended or adjusted under 35 U.S.C. 154(b) by 0 days.

(21) Appl. No.: 16/934,239

(22) Filed: Jul. 21, 2020

(65) Prior Publication Data

US 2021/0087490 A1 Mar. 25, 2021

(30) Foreign Application Priority Data

Sep. 20, 2019 (KR) .................. 10-2019-0116063

(51) Int. Cl.
| | | |
|---|---|---|
| C10M 135/10 | (2006.01) | |
| C07C 211/63 | (2006.01) | |
| C07C 317/44 | (2006.01) | |
| C07F 9/11 | (2006.01) | |
| C07F 9/54 | (2006.01) | |
| C10M 169/04 | (2006.01) | |
| C10N 20/00 | (2006.01) | |
| C10N 30/06 | (2006.01) | |

(52) U.S. Cl.
CPC ......... *C10M 135/10* (2013.01); *C07C 211/63* (2013.01); *C07C 317/44* (2013.01); *C07F 9/11* (2013.01); *C07F 9/5449* (2013.01); *C10M 169/04* (2013.01); *C10M 2203/003* (2013.01); *C10M 2219/044* (2013.01); *C10N 2020/077* (2020.05); *C10N 2030/06* (2013.01)

(58) Field of Classification Search
CPC .. C07D 471/04; C07D 207/06; C07D 285/15; C07D 233/58; C07C 255/05; C07C 309/06; C07C 311/48; C10M 105/72; C10M 105/70; C10M 2215/305; C10M 2219/0406; C10M 2219/09; C10M 2219/104; G11B 5/725
See application file for complete search history.

(56) References Cited

U.S. PATENT DOCUMENTS 8,168,830 B2 * 5/2012 Armstrong ........... B01J 20/3287
564/463
2012/0178658 A1 * 7/2012 Tredget ................ C10M 171/02
508/269

FOREIGN PATENT DOCUMENTS

| CN | 108864180 A | 6/2018 |
| JP | 2003-31270 A | 1/2003 |

(Continued)

*Primary Examiner* — Vishal V Vasisth
(74) *Attorney, Agent, or Firm* — Abelman, Frayne & Schwab

(57) ABSTRACT

Disclosed are an ionic liquid, having wear resistance maintained at low temperatures and containing a divalent cation including at least one of bis(ammonium) and bis(phosphonium) and a monovalent anion including at least one of sulfonate and phosphate, and a lubricant composition including the ionic liquid.

12 Claims, 6 Drawing Sheets

(56) References Cited

FOREIGN PATENT DOCUMENTS

| JP | 2007-204560 A | 8/2007 |
|----|---------------|--------|
| KR | 10-1973580 B | 5/2014 |
| KR | 10-2016-0150132 A | 12/2016 |
| KR | 10-2018-0116250 A | 10/2018 |
| WO | 2005035702 A1 | 4/2005 |

* cited by examiner

IONIC LIQUID CONTAINING DIVALENT CATION AND MONOVALENT ANION AND LUBRICANT COMPOSITION COMPRISING SAME

CROSS-REFERENCE TO RELATED APPLICATION

This application claims the benefit of Korean Patent Application No. 2019-0116063, filed Sep. 20, 2019, entitled "Ionic liquid containing divalent cation and monovalent anion and lubricant composition comprising the same", which is hereby incorporated by reference in its entirety into this application.

BACKGROUND OF THE DISCLOSURE

1. Technical Field

The present disclosure relates to an ionic liquid containing a divalent cation and a monovalent anion and a lubricant composition including the same.

2. Description of the Related Art

It has been reported that an ionic liquid composed of a cation and an anion has excellent thermal stability and high ionic conductivity and is stable when exposed to the ambient atmosphere (Journal of the Chemical Society, Chemical Communications, 1992, p. 965). Moreover, thorough research is ongoing into the application of an ionic liquid to various end uses, for example, electrolytes for solar cells (Japanese Patent Application Publication No. 2003-31270), extraction separation solvents, reaction solvents, etc., using the properties of the ionic liquid, such as thermal stability (low volatility, flame retardancy), high ionic density (high ionic conductivity), high heat capacity, low viscosity, and the like.

The use of such an ionic liquid as a lubricating base oil has been previously disclosed (International Publication No. 2005/035702). Since the ionic liquid is configured such that molecules are bound to each other through strong ionic bonding, it is difficult to volatilize, is flame retardant, and is highly resistant to heat and oxidation. Therefore, it has low viscosity, low evaporability, and excellent heat resistance.

Typically, the anion of the ionic liquid includes a halogen atom such as a fluorine atom. In order to design the molecular structure of an ionic liquid that is in a liquid state rather than a solid state at room temperature, an atom having high electronegativity such as halogen is introduced into the anion. This serves to reduce the electrostatic attraction between the cation and the anion through an electron delocalization effect.

However, when a halogen atom such as a fluorine atom is included, the ionic liquid is vulnerable to moisture and generates a corrosive gas and a corrosive substance when exposed to moisture. Moreover, fluorine is expensive, so ionic liquids including fluorine atoms are less economical.

SUMMARY OF THE DISCLOSURE

Accordingly, an aspect of the present disclosure is to provide an ionic liquid containing a divalent cation and an anion, having excellent corrosion resistance and wear resistance, and a lubricant composition including the same.

An embodiment of the present disclosure provides an ionic liquid containing a divalent cation including at least one of bis(ammonium) and bis(phosphonium) and a monovalent anion including at least one of sulfonate and phosphate.

Here, the bis(ammonium) may have the structure of Chemical Formula 1 below:

[Chemical Formula 1]

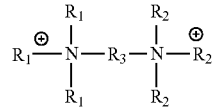

in Chemical Formula 1, each of $R_1$ and $R_2$ may be independently hydrogen, (C1-C20)hydrocarbyl, substituted (C1-C20)hydrocarbyl, (C1-C20)heterohydrocarbyl, or substituted (C1-C20)heterohydrocarbyl, and $R_3$ may be $(CH_2)_n$, where $1 \leq n \leq 20$.

In Chemical Formula 1, each of $R_1$ and $R_2$ may be independently (C1-C20)alkyl, (C2-C20)alkenyl, (C2-C20)alkynyl, (C3-C7)cycloalkyl, (C5-C20)heteroalkyl, (C6-C20)aryl, (C6-C20)ar(C1-C10)alkyl, (C1-C10)alkoxy, (C6-C20)aryloxy, (C1-C10)alkoxycarbonyl(C1-C20)alkyl, or (C1-C20)alkylcarbonyl.

In Chemical Formula 1, each of $R_1$ and $R_2$ may be independently (C1-C8)alkyl, and $R_3$ may be $(CH_2)_n$, where $1 \leq n \leq 12$.

The bis(phosphonium) may have the structure of Chemical Formula 2 below:

[Chemical Formula 2]

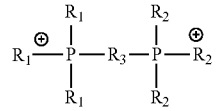

in Chemical Formula 2, each of $R_1$ and $R_2$ may be independently hydrogen, (C1-C20)hydrocarbyl, substituted (C1-C20)hydrocarbyl, (C1-C20)heterohydrocarbyl, or substituted (C1-C20)heterohydrocarbyl, and $R_3$ may be $(CH_2)_n$, where $1 \leq n \leq 20$.

In Chemical Formula 2, each of $R_1$ and $R_2$ may be independently (C1-C20)alkyl, (C2-C20)alkenyl, (C2-C20)alkynyl, (C3-C7)cycloalkyl, (C5-C20)heteroalkyl, (C6-C20)aryl, (C6-C20)ar(C1-C10)alkyl, (C1-C10)alkoxy, (C6-C20)aryloxy, (C1-C10)alkoxycarbonyl(C1-C20)alkyl, or (C1-C20)alkylcarbonyl.

In Chemical Formula 2, each of $R_1$ and $R_2$ may be independently (C1-C8)alkyl, and $R_3$ may be $(CH_2)^n$, where $1 \leq n \leq 12$.

The sulfonate may have the structure of Chemical Formula 5 below:

[Chemical Formula 5]

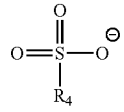

in Chemical Formula 5, $R_4$ may be (C1-C12)alkyl.

The sulfonate may have the structure of Chemical Formula 6 below:

[Chemical Formula 6]

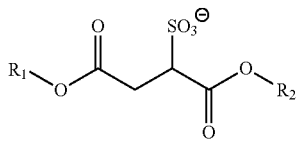

in Chemical Formula 6, each of $R_1$ and $R_2$ may be independently hydrogen, (C1-C20)hydrocarbyl, substituted (C1-C20)hydrocarbyl, (C1-C20)heterohydrocarbyl, or substituted (C1-C20)heterohydrocarbyl.

In Chemical Formula 6, each of $R_1$ and $R_2$ may be independently (C1-C20)alkyl, (C2-C20)alkenyl, (C2-C20)alkynyl, (C3-C7)cycloalkyl, (C5-C20)heteroalkyl, (C6-C20)aryl, (C6-C20)ar(C1-C10)alkyl, (C1-C10)alkoxy, (C6-C20)aryloxy, (C1-C10)alkoxycarbonyl(C1-C20)alkyl, or (C1-C20)alkylcarbonyl.

In Chemical Formula 6, each of $R_1$ and $R_2$ may be independently (C3-C10)alkyl.

The phosphate may have the structure of Chemical Formula 7 below:

[Chemial Formula 7]

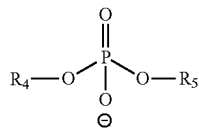

in Chemical Formula 7, each of $R_4$ and $R_5$ may be independently hydrogen, (C1-C20)hydrocarbyl, substituted (C1-C20)hydrocarbyl, (C1-C20)heterohydrocarbyl, or substituted (C1-C20)heterohydrocarbyl.

In Chemical Formula 7, each of $R_4$ and $R_5$ may be independently (C1-C20)alkyl, (C2-C20)alkenyl, (C2-C20)alkynyl, (C3-C7)cycloalkyl, (C5-C20)heteroalkyl, (C6-C20)aryl, (C6-C20)ar(C1-C10)alkyl, (C1-C10)alkoxy, (C6-C20)aryloxy, (C1-C10)alkoxycarbonyl(C1-C20)alkyl, or (C1-C20)alkylcarbonyl.

In Chemical Formula 7, each of $R_4$ and $R_5$ may be independently (C3-C10)alkyl.

Another embodiment of the present disclosure provides a lubricant composition, including the ionic liquid described above, at least one additive, and a base oil.

The lubricant composition may include 0.05 to 20 wt % of the ionic liquid and 0.1 to 50 wt % of the at least one additive.

Here, the at least one additive may be at least one selected from the group consisting of an antioxidant, a metal cleaner, an anticorrosive agent, a foam inhibitor, a pour point depressant, a viscosity modifier, a dispersant and an antiwear agent.

According to an embodiment of the present disclosure, the ionic liquid contains a specific divalent cation and a specific monovalent anion, thereby exhibiting high wear resistance and very low tendency to corrode.

DESCRIPTION OF SPECIFIC EMBODIMENTS

Figure 1:
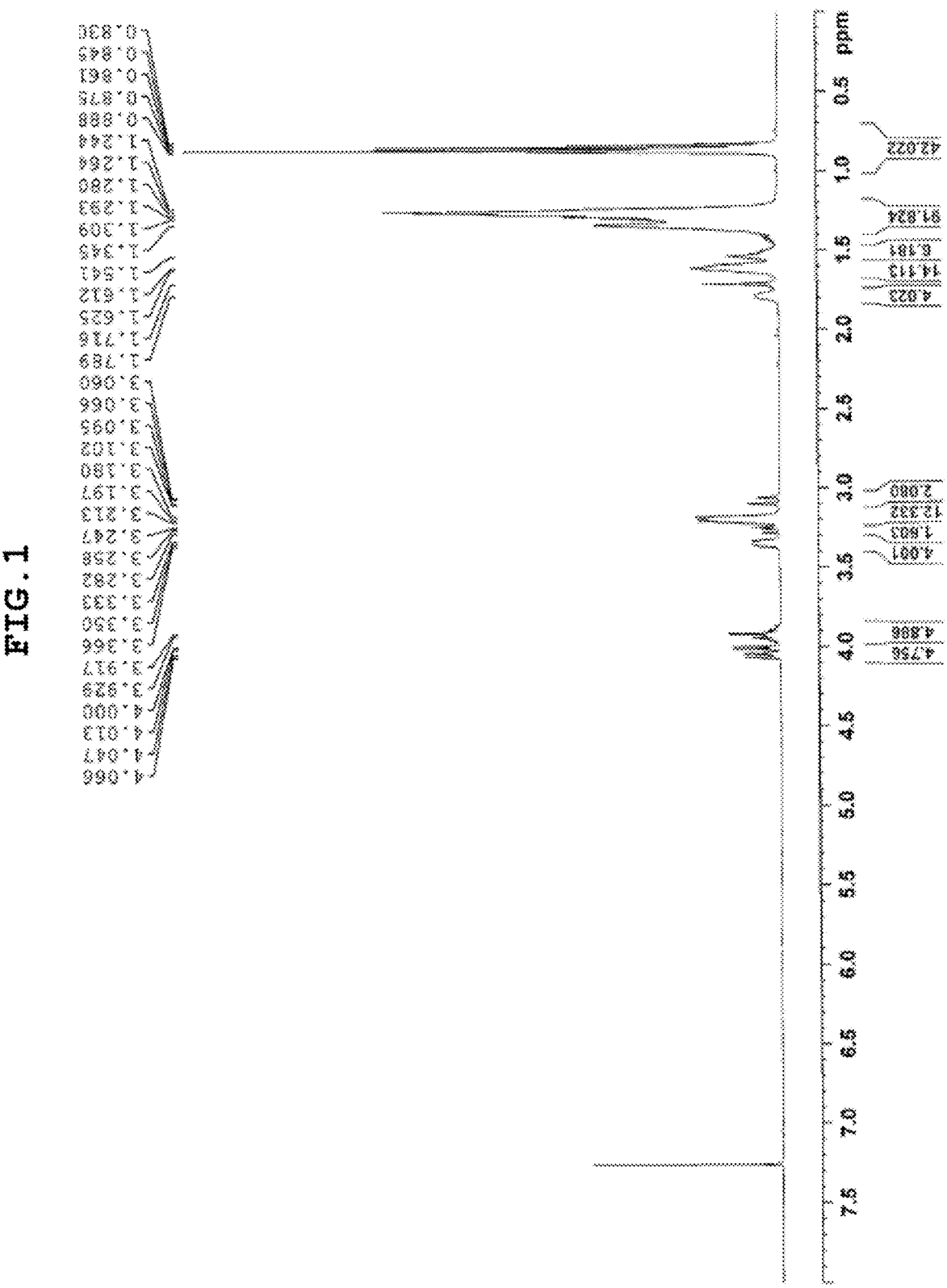
FIG. 1 shows a $^1$H-NMR spectrum of a compound containing a bis(ammonium) cation and an alkyl sulfonate anion according to an embodiment of the present disclosure.

The objectives, specific advantages and novel features of the present disclosure will become more apparent from the following detailed description and preferred embodiments associated with the accompanying drawings, but the present disclosure is not necessarily limited thereto. Furthermore, in the description of the present disclosure, it is to be noted that when a detailed description of known techniques related with the present disclosure may make the gist of the present disclosure unclear, such description will be omitted.

DEFINITION

The terms used in the present disclosure may be defined as follows.

"Hydrocarbyl" means a group containing only carbon atoms and hydrogen atoms, which may be saturated or unsaturated and may be linear, branched or cyclic. Here, "cyclic" may include both aromatic and non-aromatic.

"Substituted hydrocarbyl" means a hydrocarbyl substituted with at least one substituent.

"Heterohydrocarbyl" is a hydrocarbyl in which at least one of carbon atoms is replaced with a hetero atom, and examples of the hetero atom may include O, S, N, B, Si and P. For example, a hetero ring in which at least one carbon atom in an aromatic ring is replaced with a hetero atom may also be included in heterohydrocarbyl.

"Substituted heterohydrocarbyl" means a heterohydrocarbyl substituted with at least one substituent.

"Alkyl" refers to a saturated linear or branched hydrocarbon. For example, (C1-C6)alkyl includes a linear or branched group of 1 to 6 carbon atoms. Examples of the alkyl group may include, but are not limited to, methyl, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, and the like.

"Alkenyl" refers to an unsaturated linear or branched hydrocarbon having at least one carbon-carbon double bond.

For example, (C2-C6)alkenyl includes a linear or branched group of 2 to 6 carbon atoms. Examples of the alkenyl group may include, but are not limited to, vinyl, allyl, butenyl, pentenyl, and the like.

"Alkynyl" refers to an unsaturated linear or branched hydrocarbon having at least one carbon-carbon triple bond. For example, (C2-C6)alkynyl includes a linear or branched group of 2 to 6 carbon atoms. Examples of the alkynyl group may include, but are not limited to, ethynyl, propynyl, butynyl, pentynyl, hexynyl, methylpropynyl, and the like.

With regard to "cycloalkyl", (C3-C6)cycloalkyl refers to a monocyclic saturated hydrocarbon group of 3 to 6 carbon atoms. Examples of the cycloalkyl group may include, but are not limited to, cyclohexyl, cyclopentyl, cyclobutyl and cyclopropyl.

"Alkoxy" refers to a linear or branched alkyl group attached to oxygen (alkyl-O—). For example, (C1-C6) alkoxy includes an alkyl group of 1 to 6 carbon atoms. Examples of the alkoxy group may include, but are not limited to, methoxy, ethoxy, isopropoxy, and the like.

"Alkoxyalkyl" refers to a linear or branched alkyl group attached to oxygen and to a second linear or branched alkyl group (alkyl-O-alkyl-). For example, (C1-C6)alkoxy(C1-C6)alkyl includes respective alkyl groups containing 1 to 6 carbon atoms. Examples of the alkoxyalkyl group may include, but are not limited to, methoxymethyl, 2-methoxyethyl, 1-methoxyethyl, 2-methoxypropyl, ethoxymethyl, 2-isopropoxyethyl, and the like.

"Alkoxycarbonyl" refers to a linear or branched alkyl group attached to oxygen and to a carbonyl group (alkyl-O—C(O)-alkyl). For example, (C1-C6)alkoxycarbonyl includes an alkyl group containing 1 to 6 carbon atoms. Examples of the alkoxycarbonyl group may include, but are not limited to, methoxycarbonyl, ethoxycarbonyl, t-butoxycarbonyl, and the like.

"Alkylcarbonyl" refers to a linear or branched alkyl group attached to a carbonyl group (alkyl-C(O)—). For example, (C1-C6)alkylcarbonyl means an alkylcarbonyl group containing 1 to 6 carbon atoms. Examples of the alkylcarbonyl group may include, but are not limited to, acetyl, propanoyl, isopropanoyl, butanoyl, and the like.

Ionic Liquid

According to the present disclosure, the ionic liquid may contain a divalent cation including bis(ammonium) and/or bis(phosphonium) and a monovalent anion including sulfonate and/or phosphate.

Divalent Cation

An ionic liquid containing a divalent cation is richer in charge and has higher polarity than an ionic liquid containing a monovalent cation. Due to the strong polarity thereof, the ionic liquid containing the divalent cation has a strong interaction with a metal surface, and is advantageous in forming a thin film capable of acting as a protective film on a metal surface subjected to friction.

When a conventional ionic liquid containing a monovalent cation forms a protective film on a metal surface, the protective film is provided in the form of a double layer in a direction perpendicular to the metal surface. Since the ionic liquid containing the divalent cation has a stronger interionic interaction, when forming a protective film on a metal surface, the formation of a thicker protective film (i.e. a lubricating film) composed of multiple layers is possible.

Ionic liquids containing divalent cations have higher liquid density, a higher decomposition temperature (Td), a higher glass transition temperature (Tg), a higher melting point (Tm) and higher shear viscosity than ionic liquids containing monovalent cations.

Therefore, the ionic liquid of the present disclosure is more thermally stable because Td thereof is high, and also, because of the high density and the tendency to inhibit decomposition due to the properties of the molecular structure thereof, it is advantageous for application to fields in which local heating occurs or to the field of lubricants (especially those used at high temperatures). In particular, the ionic liquid containing the divalent cation of the present disclosure has high shear viscosity, and is thus effective at reducing loss of viscosity of oil due to shear stress. Specifically, since the ionic liquid containing the divalent cation of the present disclosure has high viscosity, it reduces loss of viscosity of oil in areas in which mechanical movement is severe, so it has superior wear resistance compared to the ionic liquid containing the monovalent cation.

In an exemplary embodiment, the bis(ammonium) of the present disclosure may have the structure of Chemical Formula 1 below.

[Chemical Formula 1]

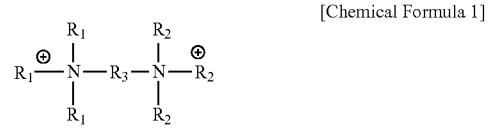

In Chemical Formula 1, each of $R_1$ and $R_2$ may be independently hydrogen, (C1-C20)hydrocarbyl, substituted (C1-C20)hydrocarbyl, (C1-C20)heterohydrocarbyl, or substituted (C1-C20)heterohydrocarbyl. $R_3$ may be $(CH_2)^n$, where $1 \leq n \leq 20$.

Also, in Chemical Formula 1, $3R_1$s are each independently the same as or different from each other, and $3R_2$s are each independently the same as or different from each other.

Also, in Chemical Formula 1, each of $R_1$ and $R_2$ may be independently (C1-C20)alkyl, (C2-C20)alkenyl, (C2-C20)alkynyl, (C3-C7)cycloalkyl, (C5-C20)heteroalkyl, (C6-C20)aryl, (C6-C20)ar(C1-C10)alkyl, (C1-C10)alkoxy, (C6-C20)aryloxy, (C1-C10)alkoxycarbonyl(C1-C20)alkyl, or (C1-C20)alkylcarbonyl.

Also, in Chemical Formula 1, each of $R_1$ and $R_2$ may be independently (C1-C8)alkyl, and $R_3$ may be $(CH_2)^n$, where $1 \leq n \leq 12$.

In a specific embodiment, the bis(ammonium) may have the structure of Chemical Formula 3 below.

[Chemical Formula 3]

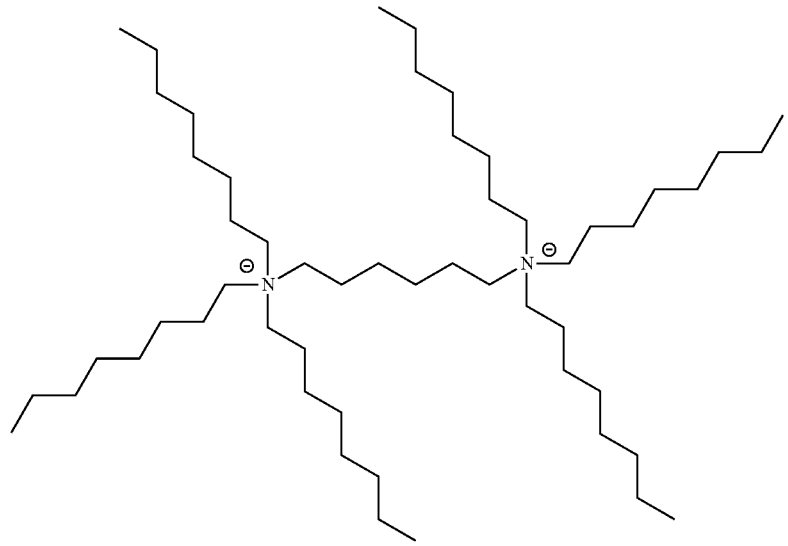

In another exemplary embodiment, the bis(phosphonium) of the present disclosure may have the structure of Chemical Formula 2 below.

[Chemical Formula 2]

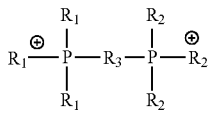

In Chemical Formula 2, each of $R_1$ and $R_2$ may be independently hydrogen, (C1-C20)hydrocarbyl, substituted (C1-C20)hydrocarbyl, (C1-C20)heterohydrocarbyl, or substituted (C1-C20)heterohydrocarbyl, and $R_3$ may be $(CH_2)_n$, where $1 \leq n \leq 20$.

Also, in Chemical Formula 2, $3R_1$s are each independently the same as or different from each other, and $3R_2$s are each independently the same as or different from each other.

Also, in Chemical Formula 2, each of $R_1$ and $R_2$ may be independently (C1-C8)alkyl, and $R_3$ may be $(CH_2)_n$, where $1 \leq n \leq 12$.

In a specific embodiment, the bis(phosphonium) may have the structure of Chemical Formula 4 below.

The specific cations having the structures of Chemical Formula 1 to Chemical Formula 4 according to the present disclosure are designed to have a specific chain length and structure, and thus may be combined with high miscibility with a specific anion according to the present disclosure. Thereby, the ionic liquid according to the present disclosure may have an excellent effect in which the physicochemical properties thereof, such as hydrophilicity/hydrophobicity, solubility, polarity, viscosity and density, are suitable for use in lubricants.

Anion

The anion of the ionic liquid according to the present disclosure is free of halogen atoms. In the ionic liquid of the present disclosure, sulfonate and/or phosphate, which are large due to substitution with a branched alkyl chain, are introduced into the anion, thereby causing an electron delocalization effect.

Through the electronic delocalization, the ionic liquid of the present disclosure may maintain a liquid state at room temperature without halogen atoms, and may exhibit hydrophobicity. Moreover, since the ionic liquid of the present disclosure is free of halogen atoms, it has corrosion resistance and excellent economic efficiency.

[Chemical Formula 4]

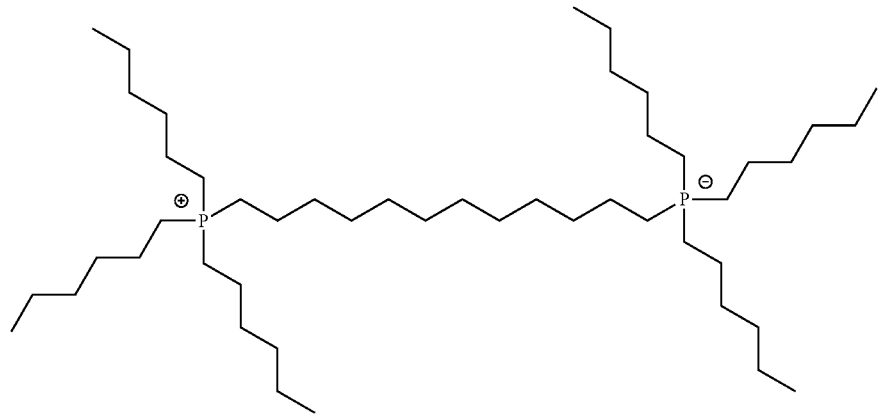

In an exemplary embodiment, the sulfonate of the present disclosure may have the structure of Chemical Formula 5 below.

[Chemical Formula 5]

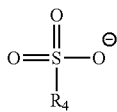

In Chemical Formula 5, $R_4$ may be (C1-C12)alkyl.

In another exemplary embodiment, the sulfonate of the present disclosure may have the structure of Chemical Formula 6.

[Chemical Formula 6]

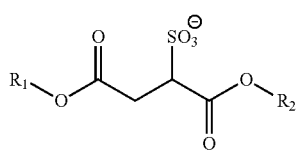

In Chemical Formula 6, each of $R_1$ and $R_2$ may be independently hydrogen, (C1-C20)hydrocarbyl, substituted (C1-C20)hydrocarbyl, (C1-C20)heterohydrocarbyl, or substituted (C1-C20)heterohydrocarbyl.

For example, in Chemical Formula 6, each of $R_1$ and $R_2$ may be independently (C1-C20)alkyl, (C2-C20)alkenyl, (C2-C20)alkynyl, (C3-C7)cycloalkyl, (C5-C20)heteroalkyl, (C6-C20)aryl, (C6-C20)ar(C1-C10)alkyl, (C1-C10)alkoxy, (C6-C20)aryloxy, (C1-C10)alkoxycarbonyl(C1-C20)alkyl, or (C1-C20)alkylcarbonyl.

Moreover, in Chemical Formula 6, each of $R_1$ and $R_2$ may be independently (C3-C10)alkyl. In a specific embodiment, the sulfonate may have the structure of Chemical Formula 8 below.

[Chemical Formula 8]

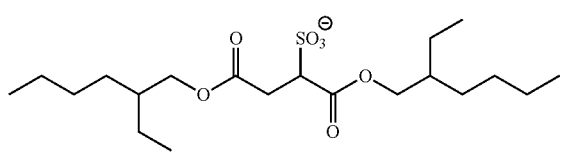

In a further exemplary embodiment, the phosphate of the present disclosure may have the structure of Chemical Formula 7 below.

[Chemical Formula 7]

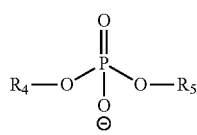

In Chemical Formula 7, each of $R_4$ and $R_5$ may be independently hydrogen, (C1-C20)hydrocarbyl, substituted (C1-C20)hydrocarbyl, (C1-C20)heterohydrocarbyl, or substituted (C1-C20)heterohydrocarbyl.

Also, in Chemical Formula 7, each of $R_4$ and $R_5$ may be independently (C1-C20)alkyl, (C2-C20)alkenyl, (C2-C20) alkynyl, (C3-C7)cycloalkyl, (C5-C20)heteroalkyl, (C6-C20)aryl, (C6-C20)ar(C1-C10)alkyl, (C1-C10)alkoxy, (C6-C20)aryloxy, (C1-C10)alkoxycarbonyl(C1-C20)alkyl, or (C1-C20)alkylcarbonyl.

In a specific embodiment, in Chemical Formula 7, each of $R_4$ and $R_5$ may be independently (C3-C10)alkyl.

In a specific embodiment, the phosphate may have a structure of Chemical Formula 9 below.

[Chemical Formula 9]

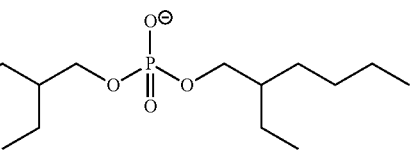

The specific anions having the structures of Chemical Formula 5 to Chemical Formula 9 according to the present disclosure are designed to have a specific chain length and structure, and thus may be combined with high miscibility with a specific cation according to the present disclosure. Thereby, the ionic liquid according to the present disclosure may have an excellent effect in which the physicochemical properties thereof, such as hydrophilicity/hydrophobicity, solubility, polarity, viscosity and density, are suitable for use in lubricants.

Lubricant Composition

In addition, the lubricant composition according to the present disclosure may be prepared by mixing a base oil with the specific ionic liquid described above and an additive in predetermined amounts.

For example, the lubricant composition according to the present disclosure may include the ionic liquid in an amount of 0.05 to 20 wt %, 0.1 to 5 wt %, or 0.5 to 5 wt %.

If the amount of the ionic liquid is less than 0.05 wt %, the miscibility between the ionic liquid and other additives may be deteriorated, or the formation of a wear-reducing film may become difficult, making it difficult to exhibit wear resistance. On the other hand, if the amount thereof exceeds 20 wt %, it is difficult to achieve a lubricant viscosity suitable for lubrication performance.

The base oil used in the lubricant composition of the present disclosure may be at least one selected from among synthetic oil, mineral oil and natural oil, and the type thereof is not particularly limited.

The synthetic oil may be selected from among ester compounds composed of aliphatic or aromatic di-, tri- or tetra-carboxylic acid and at least one of C7 to C22 alcohols; polyphenyl ether or alkyl di- or tri-phenyl ether; ester compounds composed of trimethylol propane, pentaerythritol or dipentaerythritol and C7 to C22 aliphatic carboxylic acid; ester compounds composed of a C7 to C22 alcohol and a C18 dimer acid; complex esters; and mixtures thereof. Moreover, the synthetic oil may be selected from among polyalphaolefin, alkyl naphthalene, alkylbenzene, polyglycol, silicone oil, and perfluorinated polyether.

Examples of the mineral oil may generally include those obtained by subjecting atmospheric residue resulting from atmospheric distillation of crude oil to desulfurization, hydrocracking, and classification to a desired viscosity grade, and those obtained by subjecting the atmospheric residue to solvent dewaxing or catalytic dewaxing, and as necessary, solvent extraction and hydrogenation. Also, examples of the mineral oil may include petroleum wax isomerized base oil, obtained through hydroisomerization of a petroleum wax byproduct in the dewaxing process during the production of base oil, in which atmospheric distillation residue is further subjected to vacuum distillation, classification to a desired viscosity grade, solvent refining, hydrorefining, and solvent dewaxing, GTL wax isomerized base oil, obtained by isomerizing gas-to-liquid (GTL) wax prepared through a Fisher-Tropsch process, and the like.

Examples of the natural oil may include oil converted from fatty acid derived from animal oil and vegetable oil. Examples of the animal oil may include fish oil, beef tallow, pork oil, sheep oil, butter, and the like, and examples of the vegetable oil may include sunflower seed oil, canola oil, palm oil, corn oil, cottonseed oil, rapeseed oil, linseed oil, safflower oil, oat oil, olive oil, palm oil, peanut oil, apricot oil, almond oil, avocado oil, olive oil, *camellia* oil, rice bran oil, cottonseed oil, peanut oil, walnut oil, rapeseed oil, rice bran oil, flaxseed oil, sesame oil, soybean oil, castor oil, cocoa butter, palm kernel oil, and the like.

As described above, the ionic liquid composed of the specific cation and anion according to the present disclosure may be efficiently mixed with the base oil due to the specific combination.

In addition, the lubricant composition including the ionic liquid according to the present disclosure has excellent wear resistance and corrosion resistance compared to existing lubricant compositions.

Moreover, the lubricant composition according to the present disclosure may further include at least one additive selected from among an antioxidant, a metal cleaner, an anticorrosive agent, a foam inhibitor, a pour point depressant, a viscosity modifier, a dispersant and an antiwear agent.

The antioxidant may include alkylated diphenylamine, N-alkylated phenylenediamine, hindered phenol, alkylated hydroquinone, hydroxylated thiodiphenyl ether, alkylidene bisphenol, oil soluble copper compounds, and the like. The metal cleaner may include metallic phenate, metallic sulfonate, metallic salicylate, and the like, and the anticorrosive agent may include a compound including BTA (benzotriazole). The foam inhibitor may include polyoxyalkylene polyol, etc., the pour point depressant may include poly(methyl methacrylate), etc., and the viscosity modifier may include polyisobutylene, polymethacrylate, etc. The dispersant may include polyisobutylene succinimide, polyisobutylene succinate ester, Mannich base ashless dispersants, etc., and the antiwear agent may include organic borates, organic phosphites, organic sulfur-containing compounds, zinc dialkyldithiophosphate, zinc diaryldithiophosphate, phosphosulfurized hydrocarbons, etc.

These additives are mixed with the base oil in amounts effective at imparting additional functions to the lubricant composition.

For example, the lubricant composition according to the present disclosure may include at least one additive in an amount of 0.1 to 50 wt %, 1 to 40 wt %, or 5 to 30 wt %.

Representative effective amounts of the additives are shown in Table 1 below.

TABLE 1

| Composition | Typical composition (wt %) | Preferred composition (wt %) |
|---|---|---|
| Base oil | Remainder | Remainder |
| Antioxidant | 0-5.0 | 0.01-3.0 |
| Metal cleaner | 0.1-15.0 | 0.2-8.0 |
| Anticorrosive agent | 0-5.0 | 0-2.0 |
| Foam inhibitor | 0-5.0 | 0.001-0.15 |
| Pour point depressant | 0.01-5.0 | 0.01-1.5 |
| Viscosity modifier | 0.01-10.0 | 0.25-7.0 |
| Dispersant | 0.5-5.0 | 1.0-2.5 |
| Antiwear agent | 0.01-3.0 | 0.3-2.0 |

Table 1 above shows typical effective amounts of additives commonly used in lubricant compositions. The amounts of the additives shown in Table 1 indicate the effective amounts and types of additives that are commonly used, and do not limit the scope of the present disclosure. Also, the lubricant composition according to the present disclosure may include other additives.

A better understanding of the present disclosure will be given through the following examples, which are not to be construed as limiting the scope of the present disclosure.

Example 1: Synthesis of Compound a (Bis(Ammonium) Cation & Alkyl Sulfonate Anion

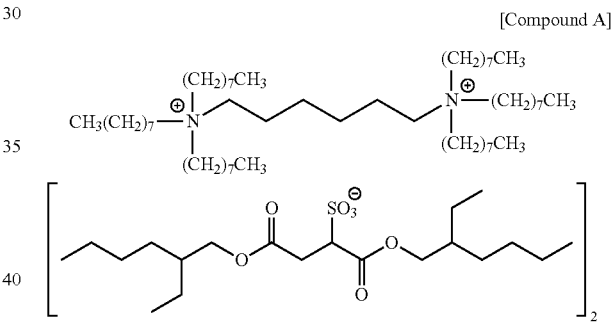

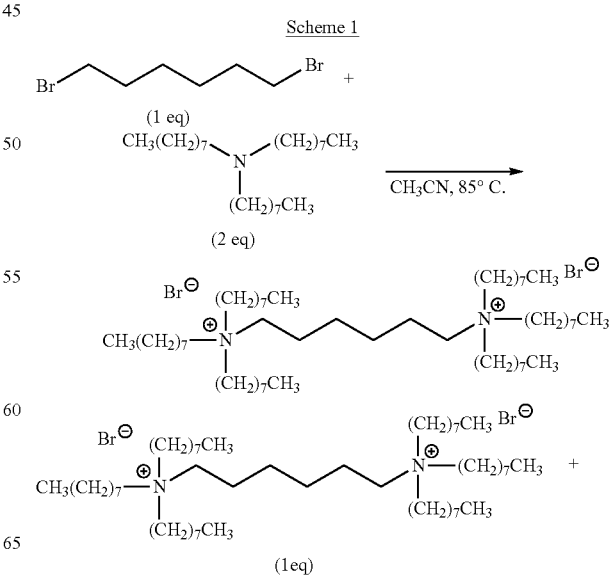

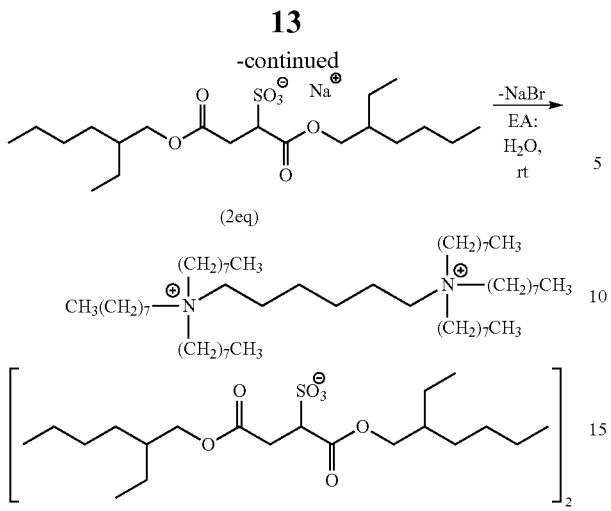

Step 1

A mixture was prepared by dissolving 4 g (16.4 mmol) of 1,6-dibromohexane and 17.4 g (49.2 mmol) of trioctylamine in 120 ml of acetonitrile (CH$_3$CN). The mixture was heated to reflux at 90° C. for 3 days and allowed to react. The reaction product was cooled to room temperature, after which the acetonitrile was removed under reduced pressure to afford a white sticky solid. In order to remove unreacted trioctylamine, 120 ml of hexane was added thereto, followed by stirring at room temperature for 1 hr, and the filtrate was removed using a filter. 120 ml of diethylether was added thereto, followed by stirring at room temperature for 1 hr, and the filtrate was removed using a filter, thus obtaining 12.5 g of a white solid (yield: 80%).

Step 2

4.7 g (10.6 mmol) of a bis-(2-ethylhexyl) sulfosuccinate sodium salt was dissolved in 40 ml of water and stirred. 5 g (5.3 mmol) of N,N-hexaoctylhexane-1,6-diaminium bromide, synthesized in step 1, was dissolved in 40 ml of ethyl acetate, and the resulting solution was added to the above sodium salt solution. The resulting mixture was stirred overnight at room temperature and then allowed to stand, after which the water layer was removed. The organic layer was washed two times with 40 ml of water, after which the ethyl acetate was removed under reduced pressure, thereby obtaining 8.3 g of compound A as a colorless clear liquid (yield: 97%). The $^1$H-NMR spectrum of compound A is shown in FIG. 1.

Example 2: Synthesis of Compound B (Bis(Ammonium) Cation & Alkyl Phosphate Anion

[Compound B]

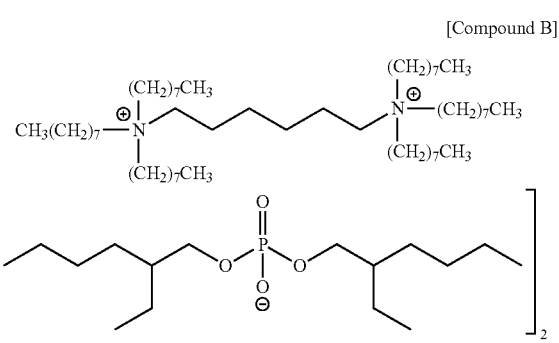

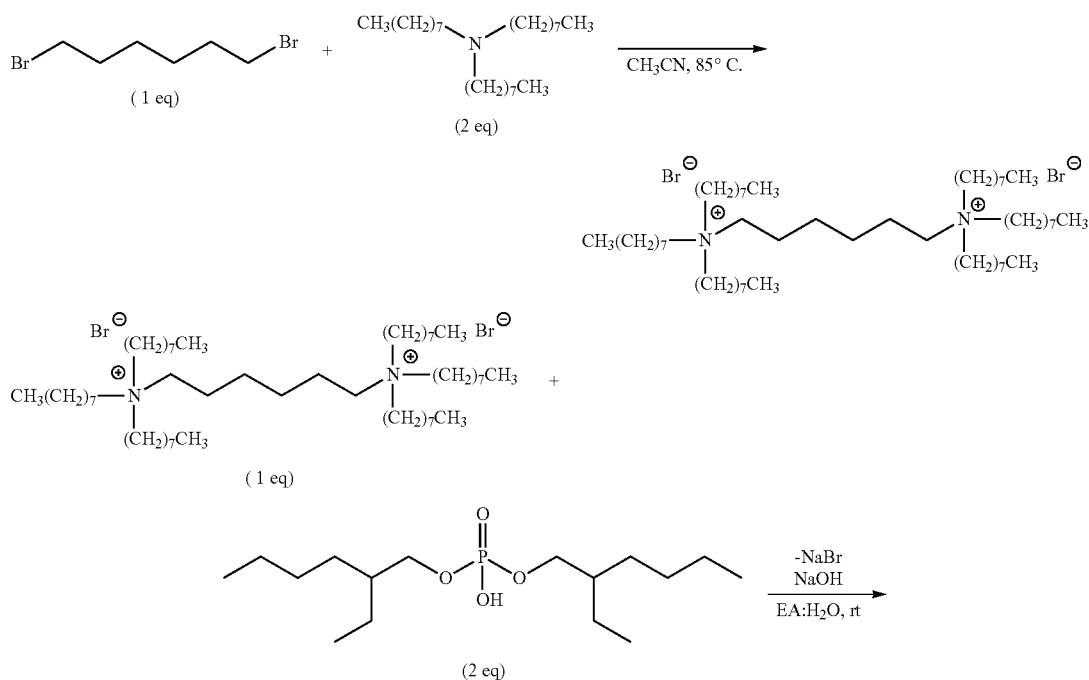

Scheme 2

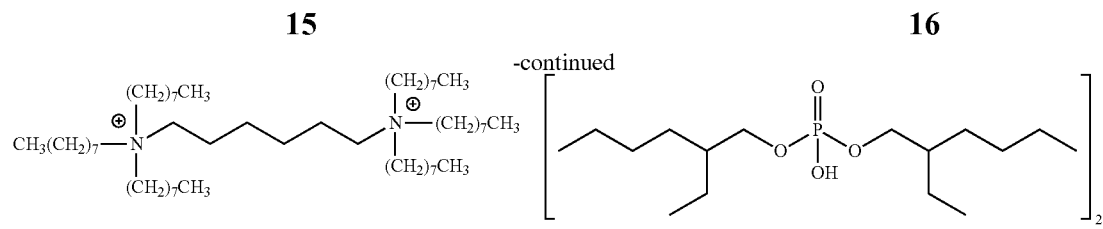

Figure 2:
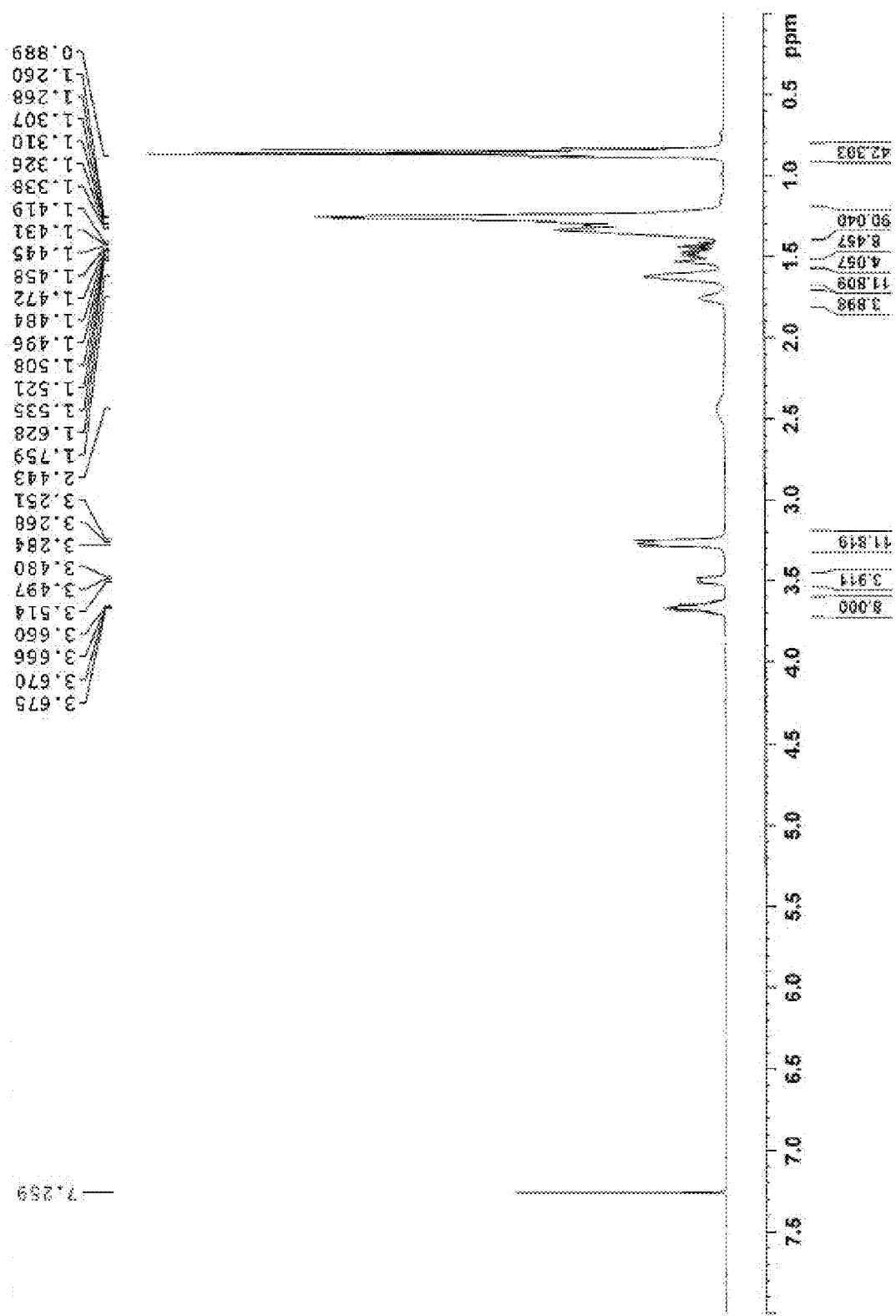
FIG. 2 shows a $^1$H-NMR spectrum of a compound containing a bis(ammonium) cation and an alkyl phosphate anion according to another embodiment of the present disclosure.

Step 1
Same as step 1 of compound A
Step 2
2.0 g (6.3 mmol) of bis-(2-ethylhexyl)phosphate was dissolved in 15 ml of water and stirred. 0.25 g (6.3 mmol) of sodium hydroxide was added thereto, and the resulting mixture was stirred at room temperature for 1 hr. 3 g (3.15 mmol) of N,N-hexaoctylhexane-1,6-diaminium bromide, synthesized in step 1, was dissolved in 30 ml of ethyl acetate, and the resulting solution was added to the above sodium salt solution. The resulting mixture was stirred overnight at room temperature and then allowed to stand, after which the water layer was removed. The organic layer was washed two times with water (15 ml), after which the ethyl acetate was removed under reduced pressure, thereby obtaining 4.3 g of compound B as an opaque liquid (yield: 95%). The $^1$H-NMR spectrum of compound B is shown in FIG. 2.

Example 3: Synthesis of Compound C
(Bis(Phosphonium) Cation & Alkyl Sulfonate Anion

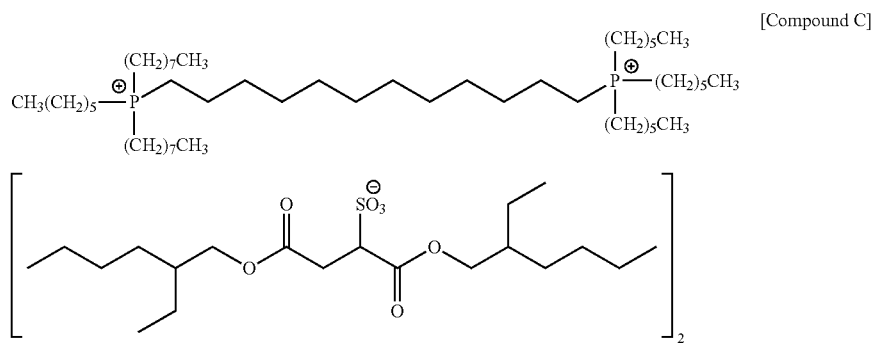

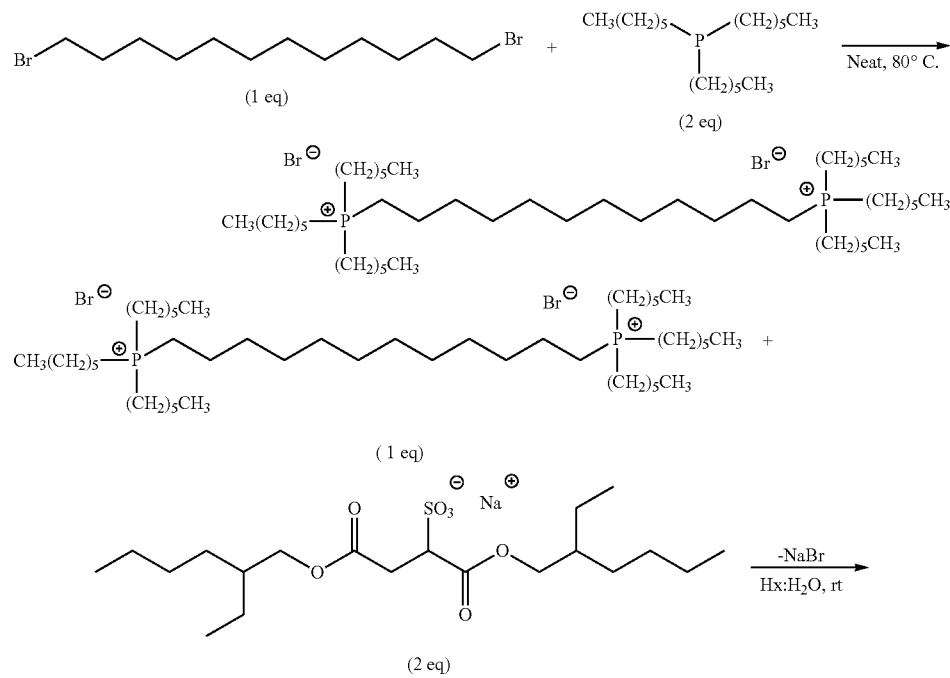

Scheme 3

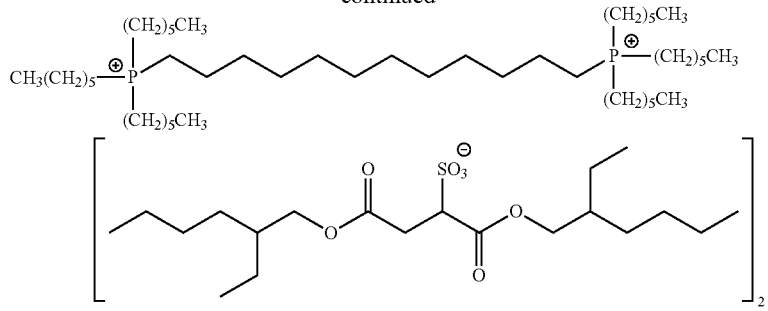

Figure 3:
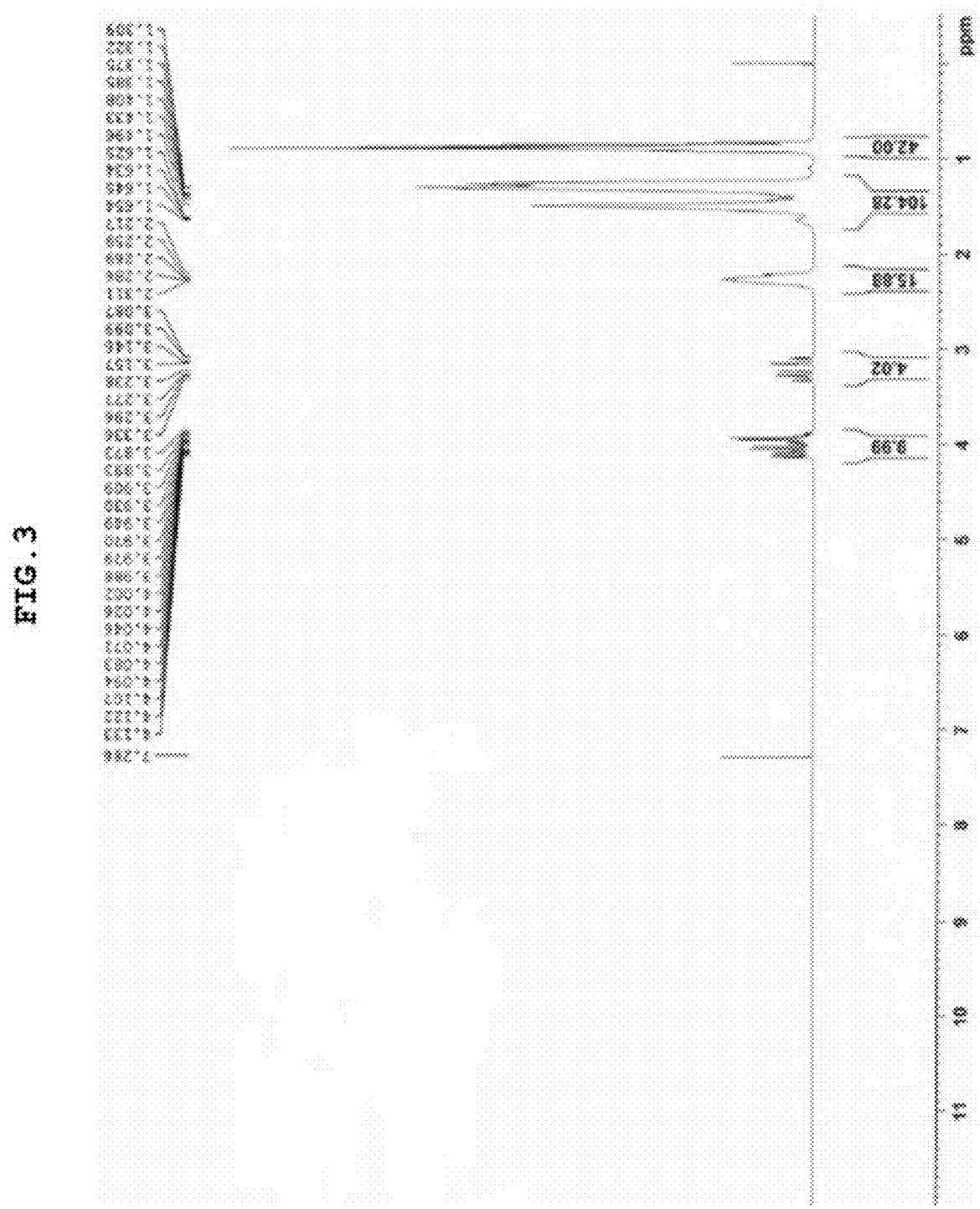
FIG. 3 shows a $^1$H-NMR spectrum of a compound containing a bis(phosphonium) cation and an alkyl sulfonate anion according to still another embodiment of the present disclosure.

2.1 g (6.3 mmol) of 1,12-dibromo-dodecane and 3.6 g (12.6 mmol) of trihexylphosphine were mixed, stirred overnight at 80° C. in a nitrogen atmosphere, and cooled to room temperature, after which the reaction product was added with 60 ml of hexane. 5.6 g (12.6 mmol) of a bis-(2-ethylhexyl)sulfosuccinate sodium salt and 6 ml of water were added thereto, and the resulting mixture was stirred overnight at room temperature and then allowed to stand. Thereafter, the water layer was removed, and the organic layer was washed two times with 10 ml of water. Thereafter, the hexane was removed under reduced pressure, thereby obtaining 9 g of compound C as a pale yellow liquid (yield: 90%). The $^1$H-NMR spectrum of compound C is shown in FIG. 3.

Example 4: Synthesis of Compound D (Bis(Phosphonium) Cation & Alkyl Phosphate Anion

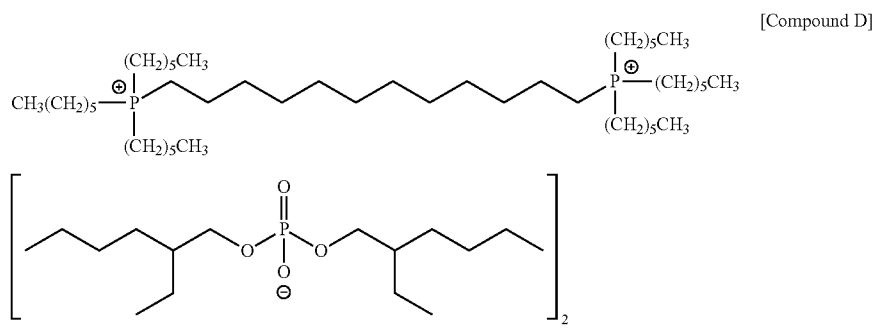

Scheme 4

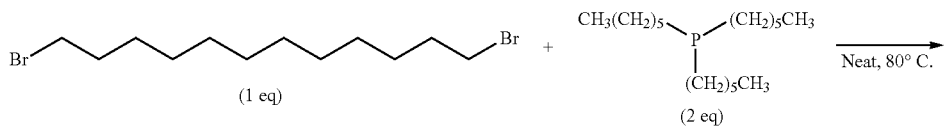

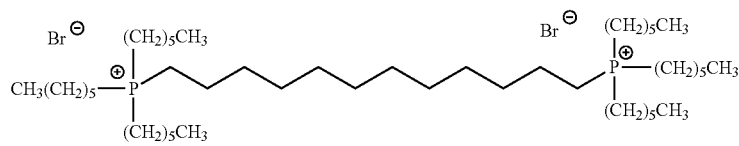

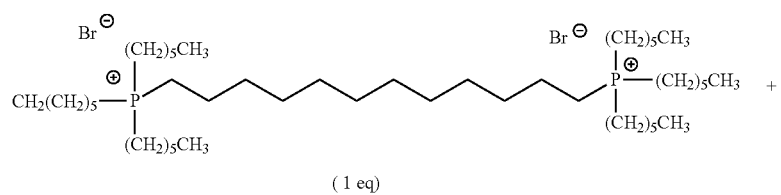

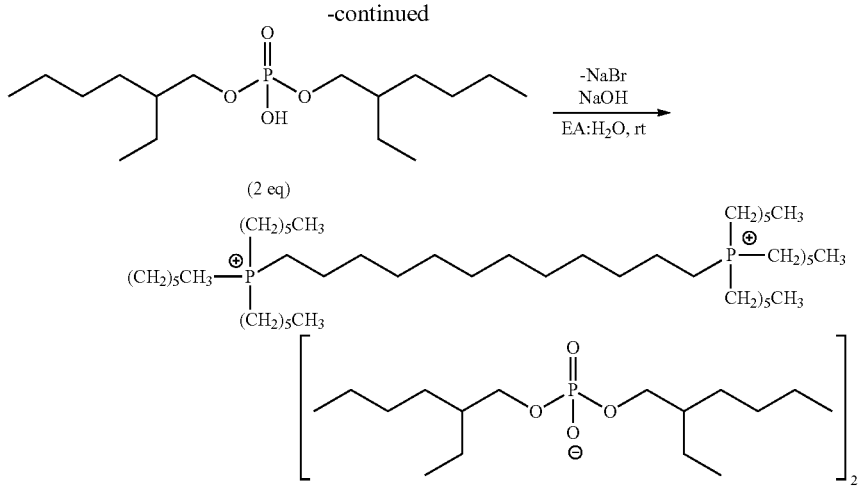

Figure 4:
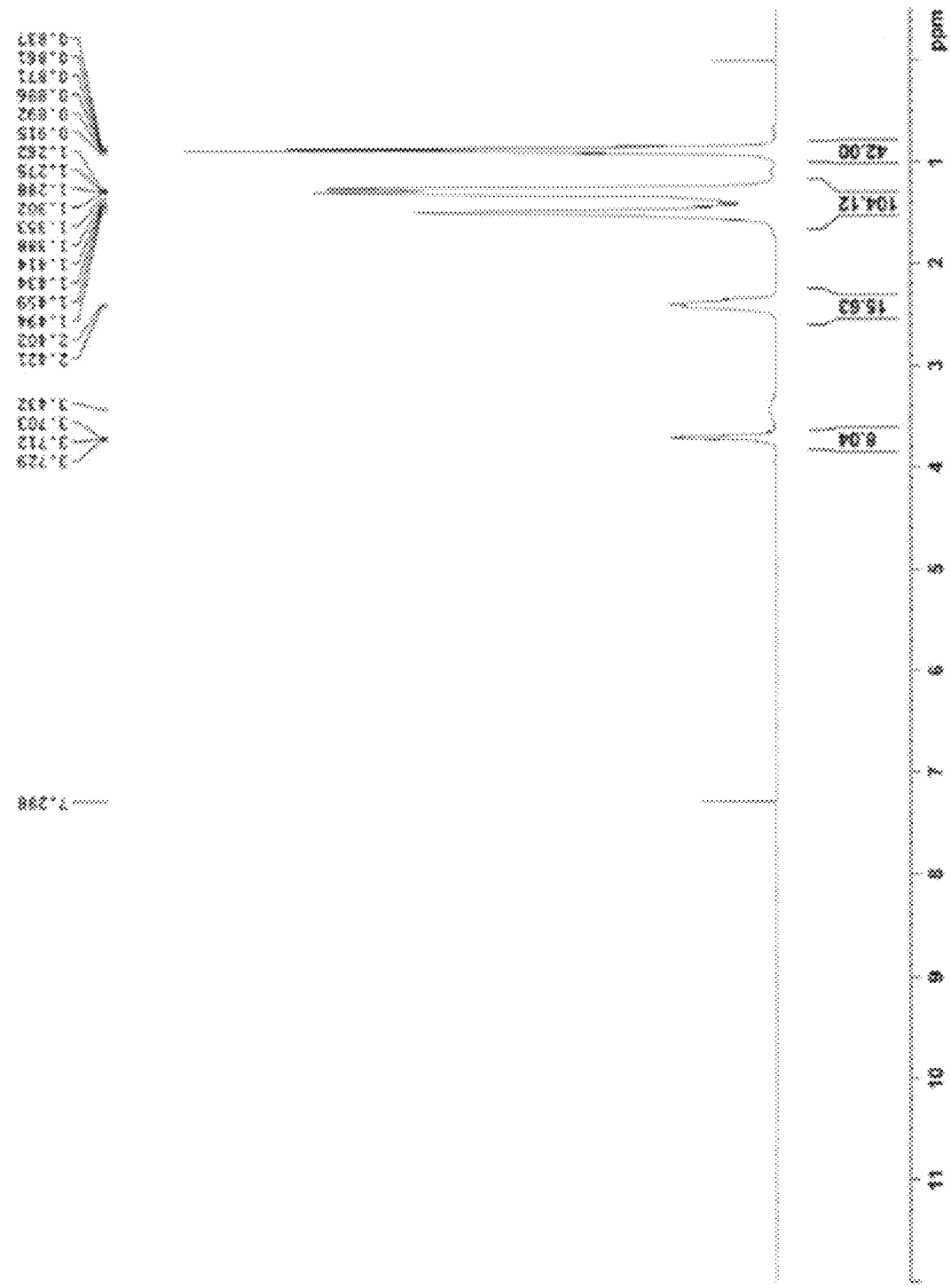
FIG. 4 shows a $^1$H-NMR spectrum of a compound containing a bis(phosphonium) cation and an alkyl phosphate anion according to yet another embodiment of the present disclosure.

2.1 g (6.3 mmol) of 1,12-dibromo-dodecane and 3.6 g (12.6 mmol) of trihexylphosphine were mixed, stirred overnight at 80° C. in a nitrogen atmosphere, and cooled to room temperature, after which the reaction product was added with 60 ml of hexane. 4.1 g (12.6 mmol) of bis-(2-ethylhexyl)phosphate, 0.5 g (12.6 mmol) of sodium hydroxide and 6 ml of water were added thereto, and the resulting mixture was stirred overnight at room temperature and then allowed to stand. Thereafter, the water layer was removed, and the organic layer was washed two times with 10 ml of water. Thereafter, the hexane was removed under reduced pressure, thereby obtaining 7.4 g of compound D as an opaque liquid (yield: 85%). The $^1$H-NMR spectrum of compound D is shown in FIG. 4.

Example 5: Synthesis of Compound E (Bis(Ammonium) Cation & Alkyl Sulfonate Anion

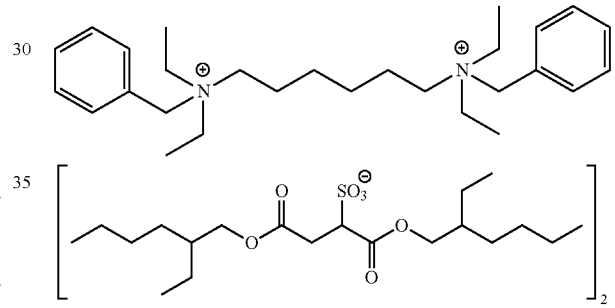

Scheme 5

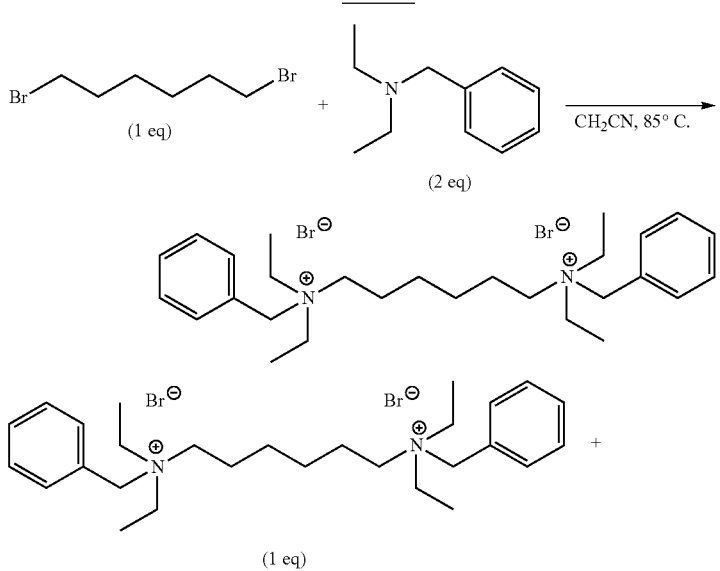

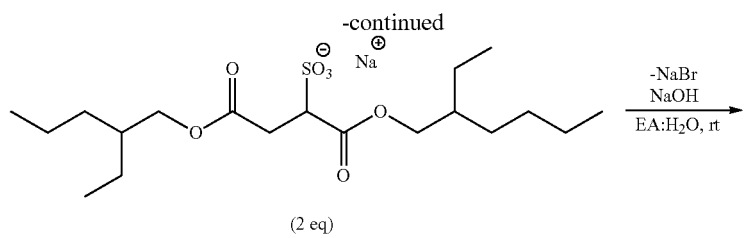

(2 eq)

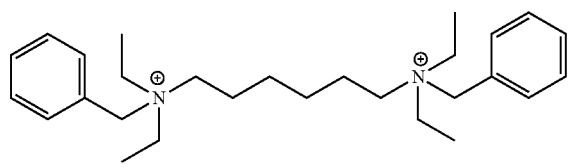

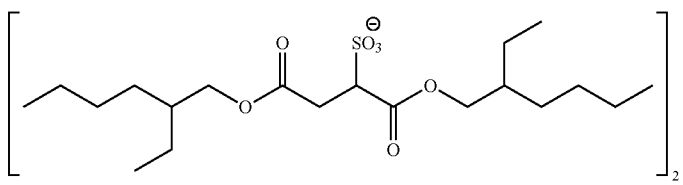

Step 1

A mixture was prepared by dissolving 1,6-dibromohexane (4 g, 16.4 mmol) and N,N-diethylbenzylamine (5.35 g, 32.8 mmol) in acetonitrile (CH₃CN, 80 ml). The mixture was heated to reflux at 90° C. for 3 days and allowed to react. The reaction product was cooled to room temperature, after which the acetonitrile was removed under reduced pressure to afford a white sticky solid. 120 ml of hexane was added thereto, followed by stirring at room temperature for 1 hr, and the filtrate was removed using a filter. 120 ml of diethylether was added thereto, followed by stirring at room temperature for 1 hr, and the filtrate was removed using a filter, thus obtaining 7.9 g of a white solid (yield: 85%).

Step 2

A bis-(2-ethylhexyl)sulfosuccinate sodium salt (7.8 g, 17.5 mmol) was dissolved in water (20 ml) and stirred. N,N-dibenzyl-N,N-tetraethylhexane-1,6-diaminium bromide (5 g, 8.8 mmol), synthesized in step 1, was dissolved in ethyl acetate (40 ml), and the resulting solution was added to the above sodium salt solution. The resulting mixture was stirred overnight at room temperature and then allowed to stand, after which the water layer was removed. The organic layer was washed two times with water (20 ml), after which the ethyl acetate was removed under reduced pressure, thereby obtaining 10.6 g of compound E as a colorless clear liquid (yield: 96%).

The NMR data for compound E was as follows.

¹H NMR (500 MHz, DMSO-$d_6$) δ 7.25 (m, 4H), 7.22 (m, 2H), 7.16 (m, 4H), 4.5 (s, 4H), 3.85 (m, 8H), 3.55 (q, 2H), 3.28-3.22 (m, 12H), 2.85 (q, 2H), 2.75 (q, 2H), 1.89 (m, 4H), 1.71 (m, 4H), 1.55 (m, 8H), 1.31-1.25 (m, 32H), 1.19 (m, 8H), 0.99 (m, 12H), 0.88 (m, 12H)

Example 6: Synthesis of Compound F (Bis(Ammonium) Cation & Alkyl Phosphate Anion

[Compound F]

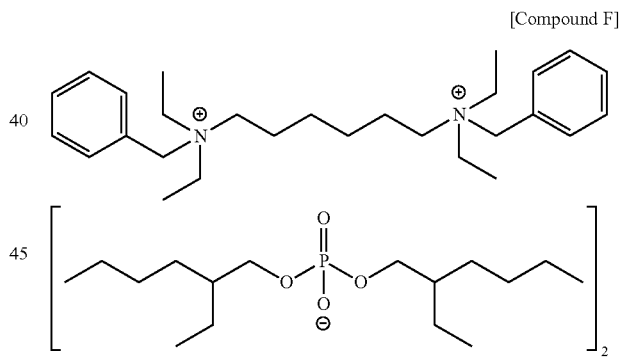

Step 1

Same as step 1 of compound E

Step 2

Bis-(2-ethylhexyl)phosphate (2.0 g, 6.3 mmol) was dissolved in water (15 ml) and stirred. Sodium hydroxide (0.25 g, 6.3 mmol) was added thereto, and the resulting mixture was stirred at room temperature for 1 hr. N,N-dibenzyl-N,N-tetraethylhexane-1,6-diaminium bromide (1.8 g, 3.15 mmol), synthesized in step 1, was dissolved in ethyl acetate (30 ml), and the resulting solution was added to the above sodium salt solution. The resulting mixture was stirred overnight at room temperature and then allowed to stand, after which the water layer was removed. The organic layer was washed two times with water (15 ml), after which the ethyl acetate was removed under reduced pressure, thereby obtaining 3.0 g of compound F as an opaque liquid (yield: 92%).

The NMR data for compound F was as follows.

$^1$H NMR (500 MHz, DMSO-$d_6$) δ 7.25 (m, 4H), 7.22 (m, 2H), 7.16 (m, 4H), 4.50 (s, 4H), 3.45 (m, 8H), 3.28-3.22 (m, 12H), 1.71 (m, 4H), 1.55 (m, 8H), 1.31-1.19 (m, 44H), 0.99 (m, 12H), 0.88 (m, 12H)

Example 7: Wear Test

<Sample Information>

Reference: viscosity grade 5W-30 engine oil

ZDDP (zinc dithiophosphate): conventional additive for reducing wear

Compound A: Ionic liquid containing divalent cation and monovalent anion prepared in Example 1

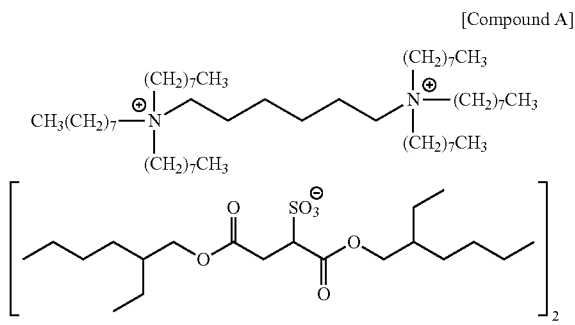

[Compound A]

Compound A': Ionic liquid containing monovalent cation and monovalent anion

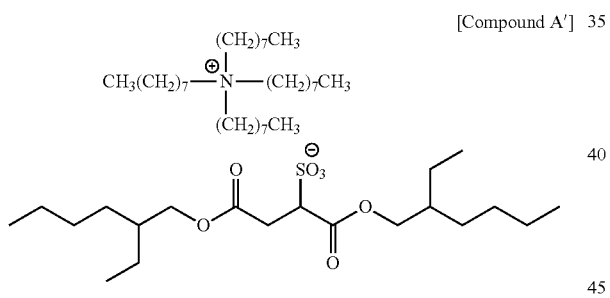

[Compound A']

<HFRR (High-Frequency Reciprocating Rig) Test>

The above samples were subjected to HFRR test. The HFRR test was performed under a load of 500 g at a temperature of 100° C. for 90 min on a ball-on-disc mode. After termination of the test, the size of wear scars was measured using a microscope, and the results thereof are shown in FIG. 5.

At 60° C., the same HFRR test was performed. The results thereof are shown in FIG. 6.

<Results>

Figure 5:
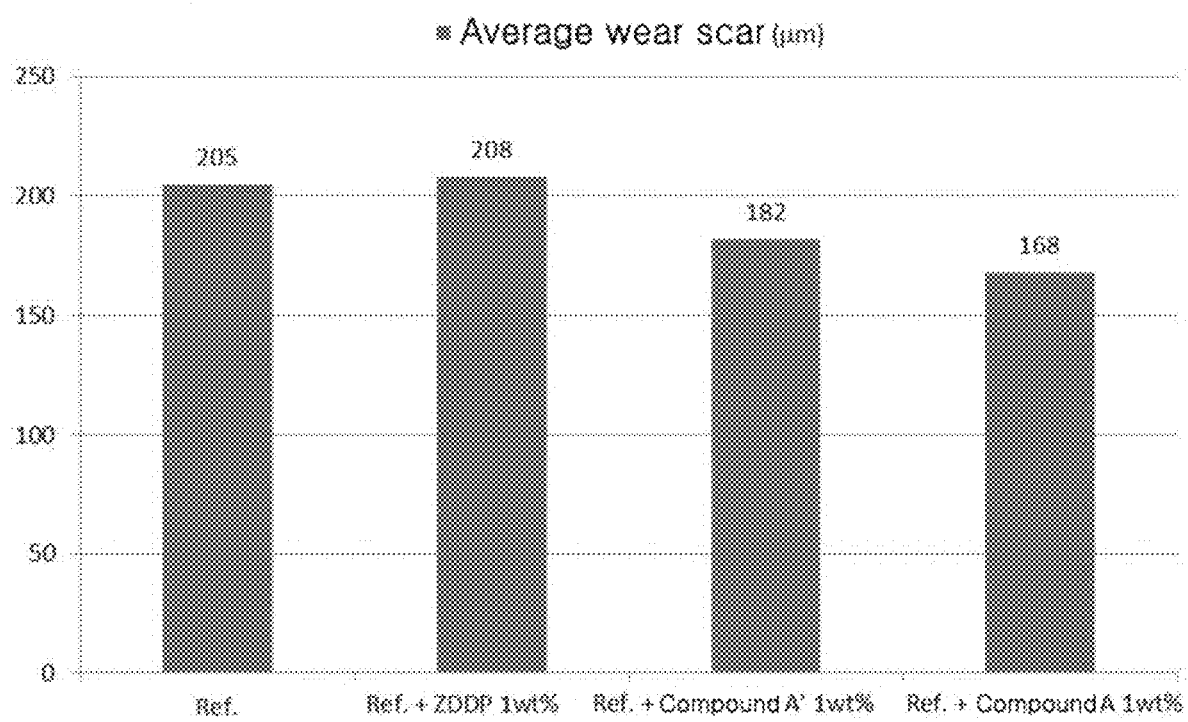
FIG. 5 is a graph showing the wear resistance at 100° C. of the ionic liquid according to an embodiment of the present disclosure.

With reference to FIG. 5, compared to the reference lubricant product not including the ionic liquid, the lubricant product including the ionic liquid containing the divalent cation and the anion was effective at reducing wear. Moreover, the lubricant product using the ionic liquid containing the divalent cation and the anion exhibited a superior wear reduction effect compared to the lubricant product using ZDDP as the conventional additive for reducing wear.

Figure 6:
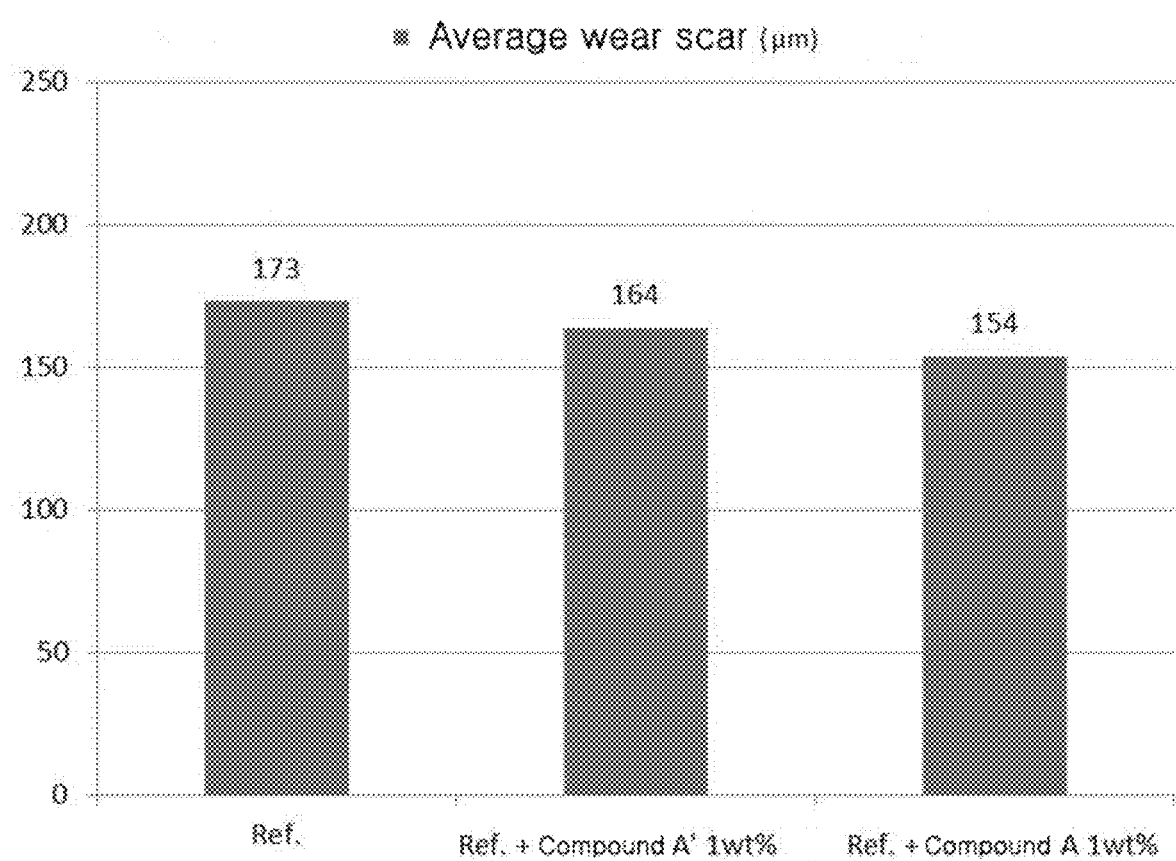
FIG. 6 is a graph showing the wear resistance at 60° C. of the ionic liquid according to an embodiment of the present disclosure.

With reference to FIGS. 5 and 6, both at a low temperature of 60° C. and a high temperature of 100° C., the lubricant product using the ionic liquid containing the divalent cation and the anion exhibited a superior wear reduction effect compared to the lubricant product using the ionic liquid containing the monovalent cation and the anion.

Although the embodiments of the present disclosure have been disclosed for illustrative purposes, those skilled in the art will appreciate that various modifications, additions and substitutions are possible, without departing from the scope and spirit of the disclosure as disclosed in the accompanying claims.

What is claimed is:

1. An ionic liquid, comprising:
   a divalent cation comprising at least one of bis(ammonium) and bis(phosphonium); and
   a monovalent anion comprising sulfonate
   wherein the sulfonate has a structure of Chemical Formula 6 below:

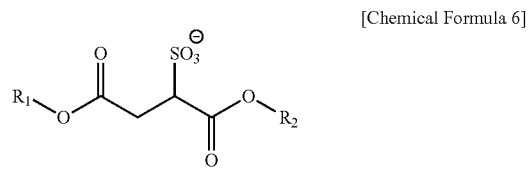

[Chemical Formula 6]

wherein in Chemical Formula 6, $R_1$ and $R_2$ are each independently hydrogen, (C1-C20)hydrocarbyl, substituted (C1-C20)hydrocarbyl, (C1-C20)heterohydrocarbyl, or substituted (C1-C20)heterohydrocarbyl.

2. The ionic liquid of claim 1, wherein the bis(ammonium) has a structure of Chemical Formula 1 below:

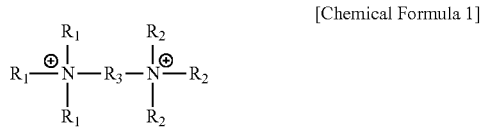

[Chemical Formula 1]

in Chemical Formula 1, $R_1$ and $R_2$ are each independently hydrogen, (C1-C20)hydrocarbyl, substituted (C1-C20)hydrocarbyl, (C1-C20)heterohydrocarbyl, or substituted (C1-C20)heterohydrocarbyl, and $R_3$ is $(CH_2)_n$, where 1≤n≤20.

3. The ionic liquid of claim 2, wherein in Chemical Formula 1, $R_1$ and $R_2$ are each independently (C1-C20)alkyl, (C2-C20)alkenyl, (C2-C20)alkynyl, (C3-C7)cycloalkyl, (C5-C20)heteroalkyl, (C6-C20)aryl, (C6-C20)ar(C1-C10)alkyl, (C1-C10)alkoxy, (C6-C20)aryloxy, (C1-C10)alkoxycarbonyl(C1-C20)alkyl, or (C1-C20)alkylcarbonyl.

4. The ionic liquid of claim 2, wherein in Chemical Formula 1, $R_1$ and $R_2$ are each independently (C1-C8)alkyl, and $R_3$ is $(CH_2)_n$, where 1≤n≤12.

5. The ionic liquid of claim 1, wherein the bis(phosphonium) has a structure of Chemical Formula 2 below:

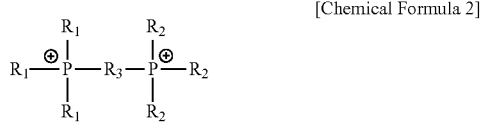

[Chemical Formula 2]

in Chemical Formula 2, $R_1$ and $R_2$ are each independently hydrogen, (C1-C20)hydrocarbyl, substituted (C1-C20)

hydrocarbyl, (C1-C20)heterohydrocarbyl, or substituted (C1-C20)heterohydrocarbyl, and $R_3$ is $(CH_2)_n$, where $1 \leq n \leq 20$.

6. The ionic liquid of claim 5, wherein in Chemical Formula 2, $R_1$ and $R_2$ are each independently (C1-C20)alkyl, (C2-C20)alkenyl, (C2-C20)alkynyl, (C3-C7)cycloalkyl, (C5-C20)heteroalkyl, (C6-C20)aryl, (C6-C20)ar(C1-C10)alkyl, (C1-C10)alkoxy, (C6-C20)aryloxy, (C1-C10)alkoxycarbonyl(C1-C20)alkyl, or (C1-C20)alkylcarbonyl.

7. The ionic liquid of claim 5, wherein in Chemical Formula 2, $R_1$ and $R_2$ are each independently (C1-C8)alkyl, and $R_3$ is $(CH_2)_n$, where $1 \leq n \leq 12$.

8. The ionic liquid of claim 1, wherein in Chemical Formula 6, $R_1$ and $R_2$ are each independently (C1-C20)alkyl, (C2-C20)alkenyl, (C2-C20)alkynyl, (C3-C7)cycloalkyl, (C5-C20)heteroalkyl, (C6-C20)aryl, (C6-C20)ar(C1-C10)alkyl, (C1-C10)alkoxy, (C6-C20)aryloxy, (C1-C10)alkoxycarbonyl(C1-C20)alkyl, or (C1-C20)alkylcarbonyl.

9. The ionic liquid of claim 1, wherein in Chemical Formula 6, $R_1$ and $R_2$ are each independently (C3-C10)alkyl.

10. A lubricant composition, comprising:
the ionic liquid of claim 1;
at least one additive; and
a base oil.

11. The lubricant composition of claim 10, comprising 0.05 to 20 wt % of the ionic liquid and 0.1 to 50 wt % of the at least one additive.

12. The lubricant composition of claim 11, wherein the at least one additive is at least one selected from the group consisting of an antioxidant, a metal cleaner, an anticorrosive agent, a foam inhibitor, a pour point depressant, a viscosity modifier, a dispersant and an antiwear agent.

* * * * *